US008420594B2

(12) United States Patent
Hulot et al.

(10) Patent No.: US 8,420,594 B2
(45) Date of Patent: Apr. 16, 2013

(54) INHIBITORS OF MRP4 AND AGENTS STIMULATING MRP4 ACTIVITY FOR THE TREATMENT OF CARDIAC DISORDERS

(75) Inventors: Jean-Sebastien Hulot, Paris Cedex (FR); Anne-Marie Lompre, Paris Cedex (FR); Yassine Sassi, Paris Cedex (FR)

(73) Assignee: INSERM (Institute de la Sante et de la Recherche Medicale), Paris (FR)

( * ) Notice: Subject to any disclaimer, the term of this patent is extended or adjusted under 35 U.S.C. 154(b) by 0 days.

(21) Appl. No.: 13/002,564

(22) PCT Filed: Jul. 17, 2009

(86) PCT No.: PCT/EP2009/059266
§ 371 (c)(1),
(2), (4) Date: Apr. 7, 2011

(87) PCT Pub. No.: WO2010/007176
PCT Pub. Date: Jan. 21, 2010

(65) Prior Publication Data
US 2011/0218232 A1 Sep. 8, 2011

(30) Foreign Application Priority Data
Jul. 17, 2008 (EP) .................... 08160652

(51) Int. Cl.
*A61K 38/00* (2006.01)
*C61P 31/00* (2006.01)

(52) U.S. Cl.
USPC ........................... 514/2; 514/44 R

(58) Field of Classification Search .................... 514/44, 514/2
See application file for complete search history.

(56) References Cited

FOREIGN PATENT DOCUMENTS

| WO | 98/48812 | 11/1998 |
|---|---|---|
| WO | 02/09761 | 2/2002 |
| WO | 2005/044244 | 5/2005 |

OTHER PUBLICATIONS

Masson et al. (Journal of Lipid Research, 2008 vol. 49:1682-1691, published in press, Apr. 27, 2008).*
Rossi et al. (Carcinogenesis, 1998 vol. 9, No. 7:1147-1152).*
Wang et al. (JBC, 2004 vol. 279, No. 28:29295-29301).*
Database Biosis [Online], Biosciences Information Service, Philadelphia, PA, US; Sep. 2001, Goldenberg Ilan et al., "Angiotensin II-induced apoptosis in rat cardiomyocyte culture: A possible role of AT1 and AT2 receptors." XP002552392.
Database Medline [Online], US National Library of Medicine (NLM), Bethesda, MD, US; Jul. 1983, Pasotti et al., "Contemporaneous administration of digitalis and dilazep to subjects with heart failure of ischemic etiology." XP002505431.
Database Medline [Online], US National Library of Medicine (NLM), Bethesda, MD, US; Oct. 2007, Birkenmeier Katrin et al., "COX-2-dependent and potentially cardioprotective effects of negative inotropic substances released after ischemia." XP002552393.
Davit Study Group Hansen et al, American Heart Journal, 134(2):s48-s52 (1997).
Gong et al., American Heart Journal, 151(1):62-68 (2006).
International Search Report in PCT/EP09/59266, dated Nov. 9, 2009.
Juhlin et al., Eur. J. Heart Failure, 6(7):909-916 (2004).
Maglich et al., J. Biol. Chem., 278(19):17277-17283 (2003).
Philip et al., Int. J. Cardiology, 122:S100 (2007).
Sanada et al., J. Cardial Failure, 13(6):S25 (2007).

* cited by examiner

*Primary Examiner* — Terra Cotta Gibbs
(74) *Attorney, Agent, or Firm* — McAndrews, Held & Malloy Ltd.

(57) ABSTRACT

The invention relates to inhibitors of Multi drug Resistant Protein 4 (MRP4) for the treatment and/or the prevention of cardiac disorders, such as acute or chronic heart failure and cardiogenic shock. The invention also relates to agents stimulating MRP4 activity for the treatment and/or the prevention of cardiac hypertrophy.

3 Claims, 2 Drawing Sheets

Figure 1:
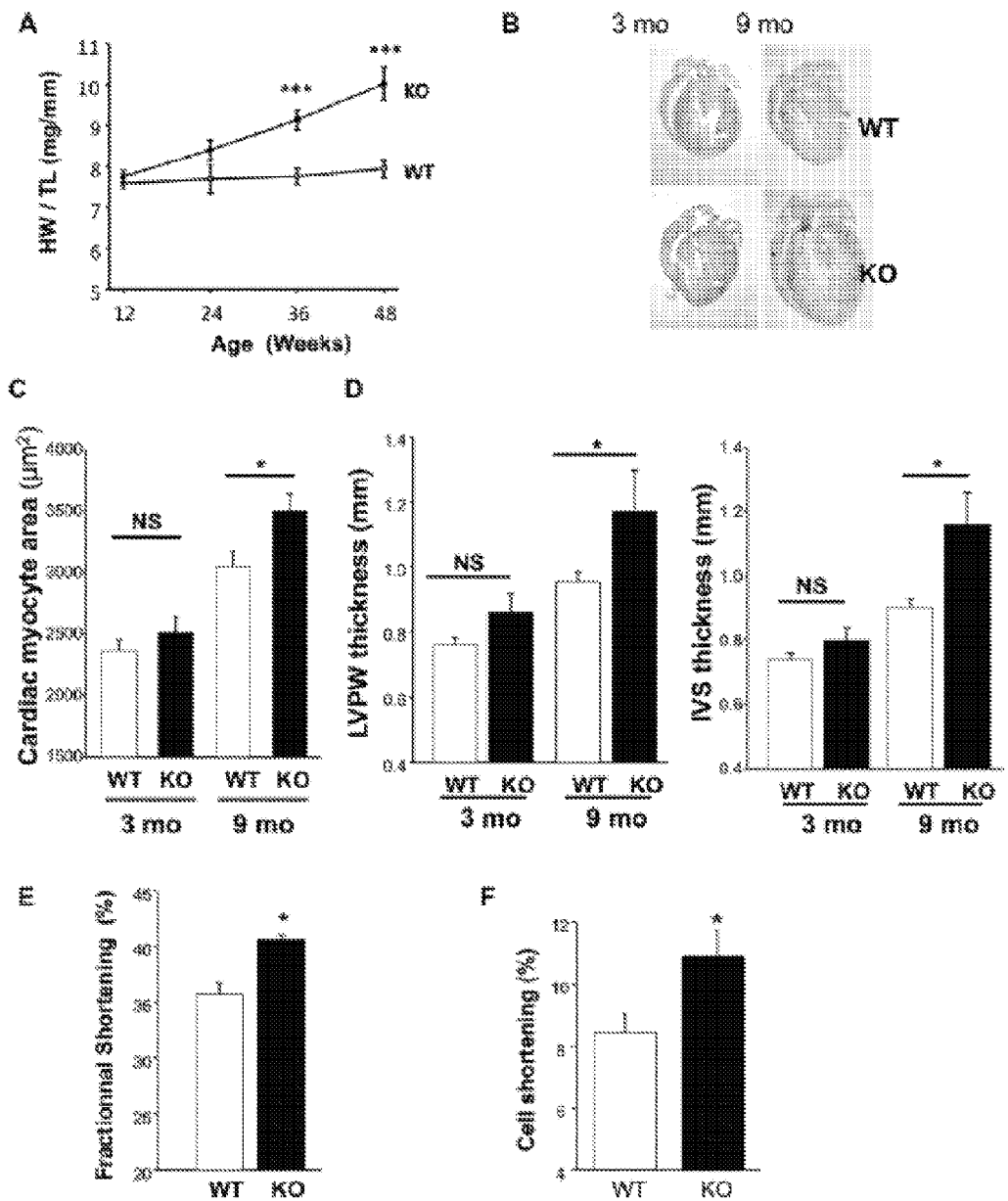

SEQUENCE LISTING

```
<160> NUMBER OF SEQ ID NOS: 13

<210> SEQ ID NO 1
<211> LENGTH: 22
<212> TYPE: DNA
```

-continued

```
<213> ORGANISM: Artificial
<220> FEATURE:
<223> OTHER INFORMATION: primer

<400> SEQUENCE: 1
ggacactgaa ctagcagaat ct                                              22

<210> SEQ ID NO 2
<211> LENGTH: 21
<212> TYPE: DNA
<213> ORGANISM: Artificial
<220> FEATURE:
<223> OTHER INFORMATION: primer

<400> SEQUENCE: 2
gtcgctgtca atgatggtgt t                                               21

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
tggcaaagtg gagattgttg                                                 20

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
cattatcggc cttgactgtg                                                 20

<210> SEQ ID NO 5
<211> LENGTH: 22
<212> TYPE: DNA
<213> ORGANISM: Artificial
<220> FEATURE:
<223> OTHER INFORMATION: primer

<400> SEQUENCE: 5
tttcaagaac ctgctagacc ac                                              22

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
ccctgcttcc tcagtctgct                                                 20

<210> SEQ ID NO 7
<211> LENGTH: 21
<212> TYPE: DNA
<213> ORGANISM: Artificial
<220> FEATURE:
<223> OTHER INFORMATION: siRNA

<400> SEQUENCE: 7
caguguucuu acacuuccut t                                               21
```

```
<210> SEQ ID NO 8
<211> LENGTH: 21
<212> TYPE: DNA
<213> ORGANISM: Artificial
<220> FEATURE:
<223> OTHER INFORMATION: siRNA

<400> SEQUENCE: 8
aggaagugua agaacacugt t                                              21

<210> SEQ ID NO 9
<211> LENGTH: 19
<212> TYPE: DNA
<213> ORGANISM: Artificial
<220> FEATURE:
<223> OTHER INFORMATION: shRNA

<400> SEQUENCE: 9
gcaaatgtgg atccgagaa                                                 19

<210> SEQ ID NO 10
<211> LENGTH: 20
<212> TYPE: DNA
<213> ORGANISM: Artificial
<220> FEATURE:
<223> OTHER INFORMATION: primer

<400> SEQUENCE: 10
caatgcagag tcggtgaagg                                                20

<210> SEQ ID NO 11
<211> LENGTH: 23
<212> TYPE: DNA
<213> ORGANISM: Artificial
<220> FEATURE:
<223> OTHER INFORMATION: primer

<400> SEQUENCE: 11
gccgcattaa gttcttcttg tct                                            23

<210> SEQ ID NO 12
<211> LENGTH: 21
<212> TYPE: DNA
<213> ORGANISM: Artificial
<220> FEATURE:
<223> OTHER INFORMATION: primer

<400> SEQUENCE: 12
tgacaatggc actttctgtt c                                              21

<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13
gcatcctcag caaagactgg                                                20
```

INHIBITORS OF MRP4 AND AGENTS STIMULATING MRP4 ACTIVITY FOR THE TREATMENT OF CARDIAC DISORDERS

The present application is filed pursuant to 35 U.S.C. 371 as a U.S. National Phase application of International Patent Application No. PCT/EP09/59266, which was filed Jul. 17, 2009, claiming the benefit of priority to European Patent Application No. 08160652.7, which was filed on Jul. 17, 2008. The entire text of the aforementioned applications is incorporated herein by reference in its entirety.

FIELD OF THE INVENTION

The invention relates to inhibitors of Multi drug Resistant Protein 4 (MRP4) for the treatment and/or the prevention of cardiac disorders, such as acute or chronic heart failure and cardiogenic shock.

The invention also relates to agents stimulating MRP4 activity for the treatment and/or the prevention of cardiac hypertrophy.

The present invention concerns gene regulation and cellular physiology in cardiomyocytes. Specifically, the invention relates to the use of inhibitors of MRP4 to block cyclic nucleotides efflux out of cells.

BACKGROUND OF THE INVENTION

Cellular proliferation and growth are two mechanisms leading to cardiac remodelling commonly observed in vascular and cardiac muscular cells in response to diverse pathological stimuli.

Hypertrophic cardiac remodelling is an adaptive response of the heart to many forms of cardiac disease, including hypertension, mechanical load abnormalities, myocardial infarction, valvular dysfunction, cardiac arrhythmias, endocrine disorders and genetic mutations in cardiac contractile protein genes. For a wide time, the hypertrophic response of cardiomyocytes has been considered as a useful compensatory state to maintain cardiac performance. However, it is now considered that such remodelling following disease-inducing stimuli is maladaptive and contributes to heart failure progression and favour arrhythmia and sudden death. Accordingly, cardiac hypertrophy has been established as an independent risk factor for cardiac morbidity and mortality.

Stereotypical pattern of changes in gene expression that include the re-expression of fetal genes are observed. Such differences are controlled by particular underlying signalling pathways. Advances in the description of signalling pathways involved in pathological cardiac remodelling and/or vascular smooth muscle cells proliferation have pointed on regulatory pathways controlled by cyclic nucleotides. Cyclic nucleotides, namely adenosine 3',5'-monophosphate (cAMP) and cyclic guanosine 3',5'-monophosphate (cGMP), are key second messengers acting as negative regulators of smooth muscle cells proliferation. The synthesis of cyclic AMP or cyclic GMP in cells is catalyzed by the adenylyl or guanylyl cyclase enzymes, respectively (McDonald & Murad, 1996; Sunahara and al., 1996). The elevation of intracellular cAMP and cGMP concentrations by cAMP or cGMP analogues, both independently inhibit rabbit vascular smooth muscle cell proliferation. (Assender J W. and al, 1992). Reexpression of constitutively active Protein kinase G (PKG) (or wild type PKG with cGMP stimulation) inhibits VSMC migration, enhances apoptosis, reduces proliferation, and decreases neointima formation after vascular injury. (Boerth N J and al., 1997; Sinnaeve P and al. 2002). cGMP (3'5' cyclic guanosin monophosphate) is also an important mediator of numerous process in muscular cells including cardiomyocytes (Silberbac M et al. 2001). Stimulation of the NO/cGMP pathway prevents cardiac hypertrophy via a negative regulation of the pro-hypertrophic genes expression (Silberbach M. et al. 2001; Barouch L A, et al. 2002). Additional insights into the role of cyclic nucleotide in preventing hypertrophic response have come from an aortic-banding model in the rat where the use of phosphodiesterase inhibitors sildenafil (which catabolizes cyclic nucleotides) results in an important cardiac hypertrophy prevention through intra-cellular cyclic nucleotides accumulation.

Following these results, focus has been made on process involved in cyclic nucleotides elimination. These cyclic nucleotides can be degraded by specific members of the phosphodiesterase (PDE) superfamily that are responsible for the hydrolysis of intracellular cAMP and cGMP. (Rybalkin and al., 2003)

Recently, Chen et al (JBC; 2001) has reported that the cAMP and the cGMP can also be transported by active efflux transporters, namely the multidrug resistance proteins (MRP) MRP4 and MRP5, encoded by the ATP-Binding Cassette transporters class C (ABCC) 4 and ABCC5 genes respectively. Among this transporter family, MRP4 and MRP5 shows high affinity for cAMP and cGMP. To date, however, the physiological function of these proteins remains unclear. Recently, MRP4 and MRP5 were identified as ATP-dependent export pumps for cyclic nucleotides (Jedlitschky and al., 2000; Chen and al., 2001) and it has been shown that MRP4 and MRP5 are expressed in the porcine coronary and pulmonary arteries (Mitani et al; 2003).

SUMMARY OF THE INVENTION

The instant application formally demonstrates for the first time that (1) MRP4 is expressed and functional in cardiomyocytes and (2) that cAMP-mediated effects in cardiomyocytes may be promoted by inhibiting MRP4. Because MRP4 is also present in the cardiomyocyte and that regulation of the cAMP level controls cardiac growth, MRP4 is therefore a target for cardiac remodeling.

The invention relates to an inhibitor of MRP4 for the treatment of a cardiac disorder selected from the group consisting of acute heart failure, and cardiogenic shock.

The invention relates to a method for treating a cardiac disorder selected from the group consisting of acute heart failure, chronic heart failure and cardiogenic shock, in a subject in need thereof comprising administering to the subject a therapeutically effective amount of a pharmaceutical composition comprising an inhibitor of MRP4.

The invention also relates to the use of an inhibitor of MRP4 for the manufacture of a medicament for promoting the contractilie activity of cardiomyocytes.

The invention also relates to an agent stimulating MRP4 activity for the treatment and/or the prevention of cardiac hypertrophy.

The invention relates to an agent stimulating MRP4 activity for the treatment of chronic heart failure.

The invention relates to a method for treating cardiac hypertrophy in a subject in need thereof comprising administering to the subject a therapeutically effective amount of a pharmaceutical composition comprising an agent stimulating MRP4 activity.

The invention also relates to the use of an agent stimulating MRP4 activity for the manufacture of a medicament for inhibiting the hypertrophic response of cardiomyocytes.

DETAILED DESCRIPTION OF THE INVENTION

Definitions

The term "MRP4" has its general meaning in the art and refers to the Multidrug Resistance Protein 4. MRP4 is also designated as ABCC4 protein, ATP-binding cassette, sub-family C(CFTR/MRP), member 4, EST 170205, MRP/cMOAT-related ABC transporter (MOAT-B), Multi-specific organic anion transporter-B (MOATB), Multidrug resistance-associated protein 4 in the art. The term may include naturally occurring MRP4s and variants and modified forms thereof. The term may also refer to fusion proteins in which a domain from MRP4 that retains at least one MRP4 activity is fused, for example, to another polypeptide (e.g., a polypeptide tag such as are conventional in the art). The MRP4 can be from any source, but typically is a mammalian (e.g., human and non-human primate) MRP4, particularly a human MRP4. An exemplary native MRP4 amino acid sequence is provided in GenPept database under accession number AAH41560 and an exemplary native nucleotide sequence encoding for MRP4 is provided in GenBank database under accession number NM_005845.

The expression "inhibitor of MRP4" should be understood broadly, it encompasses inhibitors of the MRP4 mediated cellular efflux of cyclic nucleotides, hereafter called MRP4 activity, and inhibitors of the expression of MRP4.

An "inhibitor of expression" refers to a natural or synthetic compound that has a biological effect to inhibit or significantly reduce the expression of a gene. Consequently an "inhibitor of MRP4 expression" refers to a natural or synthetic compound that has a biological effect to inhibit or significantly reduce the expression of the gene encoding for the MRP4 gene.

As used herein, the terms "selective inhibitor of MRP4" refer to an inhibitor which is selective for MRP4 as compared with the other Multidrug Resistance Proteins (MRPs) such as MRP1, MRP2, MRP3, MRP5, MRP6, MRP7, MRP8, MRP9, MRP10, MRP11, MRP12 and MRP13. By "selective" it is meant that Ki of the inhibitor for MRP4 is at least 5-fold, preferably 10-fold, more preferably 25-fold, still preferably 100-fold lower than the Ki for other MRPs. The Ki of an inhibitor of MRP4 may be determined using various methods well known in the art.

The expression "agent stimulating MRP4 activity" should be understood broadly, it encompasses agents which stimulate the MRP4 mediated cellular efflux of cyclic nucleotides, hereafter called MRP4 activity, and agents which stimulate the expression of MRP4. Typically, examples of agents stimulating MRP4 expression are nuclear hormone receptor constitutive androstane receptor agonist: 1,4-bis[2-(3,5-dichloropyridyloxy)]benzene (TCPOBOP) (Masson D, 2008), 6-(4-chlorophenyl)imidazo[2,1-b][1,3]thiazole-5-carbaldehyde O-(3,4-dichlorobenzyl)oxime (CITCO) (Maglich J M 2003). Alternatively another example of agents stimulating MRP4 expression is a genetic vector (e.g. plasmids, viral vector . . . ) expressing MRP4. Typically this vector may be delivered specifically to the heart.

The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

As used herein, the term "subject" denotes a mammal, such as a rodent, a feline, a canine, and a primate. Preferably, a subject according to the invention is a human.

In its broadest meaning, the term "treating" or "treatment" refers to reversing, alleviating, inhibiting the progress of, or preventing the disorder or condition to which such term applies, or one or more symptoms of such disorder or condition.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Methods and Uses

The invention relates to an inhibitor of MRP4 for the treatment of a cardiac disorder selected from the group consisting of acute heart failure, chronic heart failure and cardiogenic shock. The invention relates to a method for treating a cardiac disorder selected from the group consisting of acute heart failure, chronic heart failure and cardiogenic shock, in a subject in need thereof comprising administering to the subject a therapeutically effective amount of a pharmaceutical composition comprising an inhibitor of MRP4.

The invention also relates to the use of an inhibitor of MRP4 for the manufacture of a medicament for stimulating cardiac contractility.

The invention also relates to an agent stimulating MRP4 activity for the treatment and/or the prevention of cardiac hypertrophy. The invention relates to a method for treating cardiac hypertrophy in a subject in need thereof comprising administering to the subject a therapeutically effective amount of a pharmaceutical composition comprising an agent stimulating MRP4 activity. The invention also relates to the use of an agent stimulating MRP4 activity for the manufacture of a medicament for inhibiting the hypertrophic response of cardiomyocytes.

The present invention also provides methods and compositions (such as pharmaceutical compositions) for treating and/or preventing cardiac hypertrophy, acute and chronic heart failure, and cardiogenic shock.

Typically the treatment may improve one or more symptoms of cardiac hypertrophy or heart failure, such as providing increased exercise capacity, increased blood ejection volume, left ventricular end diastolic pressure, left ventricular end systolic and diastolic dimensions, wall tension and wall thickness, quality of life, disease-related morbidity and mortality, reversal of progressive remodeling, improvement of ventricular dilation, increased cardiac output, relief of impaired pump performance, improvement in arrhythmia.

The invention also relate to the use of an inhibitor of MRP4 for promoting the growth of cardiomyocytes in vitro.

The invention also relates to a method for culturing cardiomyocytes, wherein the cardiomyocytes are cultured in the presence of an inhibitor of MRP4.

In a preferred embodiment an inhibitor of MRP4 according to the invention is a selective inhibitor of MRP4.

In one embodiment, the MRP4 inhibitor may be a low molecular weight inhibitor, e.g. a small organic molecule. Examples of MRP4 inhibitor are given in US2006/0286041, in Reid et al. (Molecular Pharmacology, 63: 1094-1103, 2003) and in Rémon et al. (J Am Soc Nephrol 13:595-603, 2002).

Small organic MRP4 inhibitors that may be used by the invention include, but are not limited to compounds selected from the group consisting of N-Acetyl-dinitrophenyl-Cysteine, Benzbromarone, Cholate, Diclofenac, Dipyrimadole, Dehydroepiandrosterone 3-glucuronide, Dehydroepiandrosterone 3-sulphate, Dilazep, Dinitrophenyl-5-glutathione, Estradiol 17-[beta]-glucuronide, Estradiol 3,17-disulphate, Estradiol 3-glucuronide, Estradiol 3-sulphate, Estrone 3-sulphate, Flurbiprofen, Folate, N5-formyl-tetrahydrofolate, Glycocholate, Glycohthocholic acid sulphate, Ibuprofen, Indomethacin, Indoprofen, Ketoprofen, Lithocholic acid sulphate, Methotrexate, MK571 (([pound])-3-[[[3-[2-(7-Chloro-2-quinohnyl)ethenyl]phenyl]-[[3-dimethylamino)-3-oxopropyl]thio]methyl]thio]-propanoic acid), [alpha]-Naphthyl-[beta]-D-glucuronide, Nitrobenzyl mercaptopurine[pi]boside, Probenecid, PSC833, Sulfinpyrazone, Taurochenodeoxycholate, Taurocholate, Taurodeoxycholate, Taurohthocholate, Taurolithochohc acid sulphate, Topotecan, Trequinsin, Verapamil and Zap[pi]nast, optionally in the form of the racemates, the enantiomers, the diastereomers and optionally the pharmacologically acceptable acid addition salts and the hydrates thereof.

In an embodiment of the invention the inhibitor of MRP4 is not a Phosphodiesterase (PDE) inhibitor selected from the group consisting of PDE3 inhibitors, PDE4 inhibitors, PDE5 inhibitors.

In an embodiment of the invention the inhibitor of MRP4 is not selected from the group consisting of sulfated dehydroepiandrosterone, methotrexate, verapamil, ibuprofen, diclofenac, dipyridamole and dilazep.

By acid addition salts of MRP4 inhibitor, with pharmacologically acceptable acids are meant for example salts selected from the group comprising the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccmate, hydrobenzoate and hydro-p-toluenesulphonate, preferably the hydrochloride, hydrobromide, hydrosulphate, hydrophosphate, hydrofumarate and hydromethanesulphonate. Of the above-mentioned acid addition salts, the salts of hydrochloric acid, methanesulphonic acid, benzoic acid and acetic acid are particularly preferred according to the invention In another embodiment the MRP4 inhibitor is an antibody or antibody fragment that can partially or completely block the MRP4 transport activity (i.e. a partial or complete MRP4 blocking antibody or antibody fragment).

In particular, the MRP4 inhibitor may consist in an antibody directed against the MRP4, in such a way that said antibody blocks the activity of MRP4.

Antibodies directed against the MRP4 can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against MRP4 can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see, e.g., U.S. Pat. No. 4,946,778) can be adapted to produce anti-MRP4, single chain antibodies. MRP4 inhibitors useful in practicing the present invention also include anti-MRP4 fragments including but not limited to F(ab')$_2$ fragments, which can be generated by pepsin digestion of an intact antibody molecule, and Fab fragments, which can be generated by reducing the disulfide bridges of the F(ab')$_2$ fragments. Alternatively, Fab and/or scFv expression libraries can be constructed to allow rapid identification of fragments having the desired specificity to MRP4.

Humanized anti-MRP4 antibodies and antibody fragments thereof can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

In still another embodiment, the inhibitor of MRP4 is an aptamer.

Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as E. coli Thioredoxin A that are selected from combinatorial libraries by two hybrid methods (Colas et al., 1996).

Another aspect of the invention relates to selective inhibitor of MRP4 expression.

MRPs sequences showing low sequence identity (<60%) the inhibitors of MRP4 expression which may be used according to the invention advantageously provides selective inhibition of MRP4 expression, by comparison with other MRPs expression.

Inhibitors of MRP4 expression for use in the present invention may be based on anti-sense oligonucleotide constructs. Anti-sense oligonucleotides, including anti-sense RNA molecules and anti-sense DNA molecules, would act to directly block the translation of MRP4 mRNA by binding thereto and thus preventing protein translation or increasing mRNA degradation, thus decreasing the level of MRP4s, and thus activity, in a cell. For example, antisense oligonucleotides of at least about 15 bases and complementary to unique regions of the mRNA transcript sequence encoding MRP4 can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as inhibitors of MRP4 expression for use in the present invention. MRP4 expression can be reduced by contacting a subject or cell with a small double stranded RNA (dsRNA), or a vector or construct causing the production of a small double stranded RNA, such that MRP4 expression is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836). A siRNA efficiently silencing MRP4 has been developed. This siRNA will target the several MRP4 splicing variants (NM_005845, BC041560, AY081219, AF541977, AY133680, AY133679, AY133678). The sense sequence is 5'-CAGUGUUCUUA-CACUUCCUTT-3' (SEQ ID NO:7) and anti-sense: 5'-AG-GAAGUGUAAGAACACUGTT-3' (SEQ ID NO:8).

shRNAs (short hairpin RNA) can also function as inhibitors of MRP4 expression for use in the present invention. An example of short hairpin RNA according to the invention is a shRNA comprising the sequence as set forth in SEQ ID NO: 9: GCAAATGTGGATCCGAGAA.

Ribozymes can also function as inhibitors of MRP4 expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of MRP4 mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable.

Both antisense oligonucleotides and ribozymes useful as inhibitors of MRP4 expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides, siRNAs, shRNAs and ribozymes of the invention may be delivered in vivo alone or in association with a vector. In its broadest sense, a "vector" is any vehicle capable of facilitating the transfer of the antisense oligonucleotide, siRNA, shRNA or ribozyme nucleic acid to the cells and preferably cells expressing MRP4. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, 1990 and in Murry, 1991).

Preferred viruses for certain applications are the adenoviruses and adeno-associated (AAV) viruses, which are double-stranded DNA viruses that have already been approved for human use in gene therapy. Actually 12 different AAV serotypes (AAV1 to 12) are known, each with different tissue tropisms (Wu, Z Mol Ther 2006; 14:316-27). Recombinant AAV are derived from the dependent parvovirus AAV2 (Choi, V W J Virol 2005; 79:6801-07). The adeno-associated virus type 1 to 12 can be engineered to be replication deficient and is capable of infecting a wide range of cell types and species (Wu, Z Mol Ther 2006; 14:316-27). It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUCI9, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a genegun. The plasmids may be given in an aqueous solution, dried onto gold particles or in association with another DNA delivery system including but not limited to liposomes, dendrimers, cochleate and microencapsulation.

In a preferred embodiment, the antisense oligonucleotide, siRNA, shRNA or ribozyme nucleic acid sequence is under the control of a heterologous regulatory region, e.g., a heterologous promoter. The promoter can be, e.g., a smooth muscle specific promoter, such as a smooth muscle alpha actin promoter, SM22α promoter, cardiac specific promoter, such as cardiac myosin promoter (e.g., a cardiac myosin light chain 2 v promoter), troponin T promoter, or BNP promoter. The promoter can also be, e.g., a viral promoter, such as CMV promoter or any synthetic promoters. The selective inhibitor of MRP4 activity and/or expression may be administered in the form of a pharmaceutical composition, as defined below.

Preferably, said inhibitor is administered in a therapeutically effective amount.

By a "therapeutically effective amount" is meant a sufficient amount of the MRP4 inhibitor to treat and/or to prevent cardiac disorders at a reasonable benefit/risk ratio applicable to any medical treatment.

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidential with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Screening Methods

Inhibitors of MRP4 or agents stimulating MRP4 activity of the invention can be further identified by screening methods described in the state of the art. The screening methods of the invention can be carried out according to known methods.

The screening method may measure the binding of a candidate compound to MRP4, or to cells or membranes bearing MRP4, or a fusion protein thereof by means of a label directly or indirectly associated with the candidate compound. Alternatively, a screening method may involve measuring or, qualitatively or quantitatively, detecting the competition of binding of a candidate compound to the receptor with a labelled competitor (e.g., inhibitor or substrate).

For example, MRP4 cDNA may be inserted into an expression vector that contains necessary elements for the transcription and translation of the inserted coding sequence. Following vector/host systems may be utilized such as Baculovirus/Sf9 Insect Cells Retrovirus/Mammalian cell lines like HepB3, LLC-PK1, MDCKII, CHO, HEK293 Expression vector/Mammalian cell lines like HepB3, LLC-PK1, MDCKII, CHO, HEK293. Such vectors may be then used to transfect cells so that said cells express recombinant MRP4 at their membrane. It is also possible to use cell lines expressing endogenous MRP4 protein (THP-1, U937, WI-38, WI-38 (VA-13 subline), IMR-90, HEK-293).

Cells obtained as above described may be the pre-incubated with test compounds and subsequently stimulated with compounds known to elevate cellular cAMP and/or cGMP production (such as Forskolin, Isoprenaline, for cAMP and SNP for cGMP). Test compounds are screened for their ability to enhance intracellular cAMP and/or cGMP levels and reduce extracellular cAMP and/or cGMP levels.

In a further embodiment, membrane vesicles may be prepared from cell lines obtained as above described. Membrane vesicles may be then pre-incubated with test compounds. Subsequently, cAMP, ATP, and ATP regeneration systems (creatine kinase and creatine phosphate) are added to the membrane vesicles, and compounds are screened for their ability to inhibit the accumulation of cAMP inside the membrane vesicles.

Pharmaceutical Compositions

A further object of the invention relates to pharmaceutical compositions for treating cardiac disorders.

The MRP4 inhibitor or the agent stimulating MRP4 activity may be combined with pharmaceutically acceptable excipients, and optionally sustained-release matrices, such as biodegradable polymers, to form therapeutic compositions.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The MRP4 inhibitor or the agent stimulating MRP4 activity of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The MRP4 inhibitor or the agent stimulating MRP4 activity of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

The invention will further be illustrated in view of the following figures and example.

FIG. 1. MRP4 ablation is associated with progressive cardiac hypertrophy. (A) Age-dependent increase in heart weight to tibia length ratio (HW/TL), data are from >6 animals per data point±s.e.m. (B) Histology after sirius red labelling and cardiac myocytes area (C) Ventricular myocytes area from 3- and 9-month-old WT and MRP4 KO mice hearts showing cardiac hypertrophy in 9 month-old MRP4-deficient mice hearts compared to aged matched WT. (D) Echocardiography parameters showing the LVPW thickness, the IVS thickness of heart from 3- and 9 month-old MRP4 KO and WT mice (n=4-6) (*p<0.05; p<0.01; *p<0.001). (E) Fractional shortening of hearts from 9 month-old MRP4 KO mice compared to age-matched WT. (F) Percentage of shortening of ventricular myocytes isolated from 9-month-old WT and MRP4 KO mice.

Figure 2:
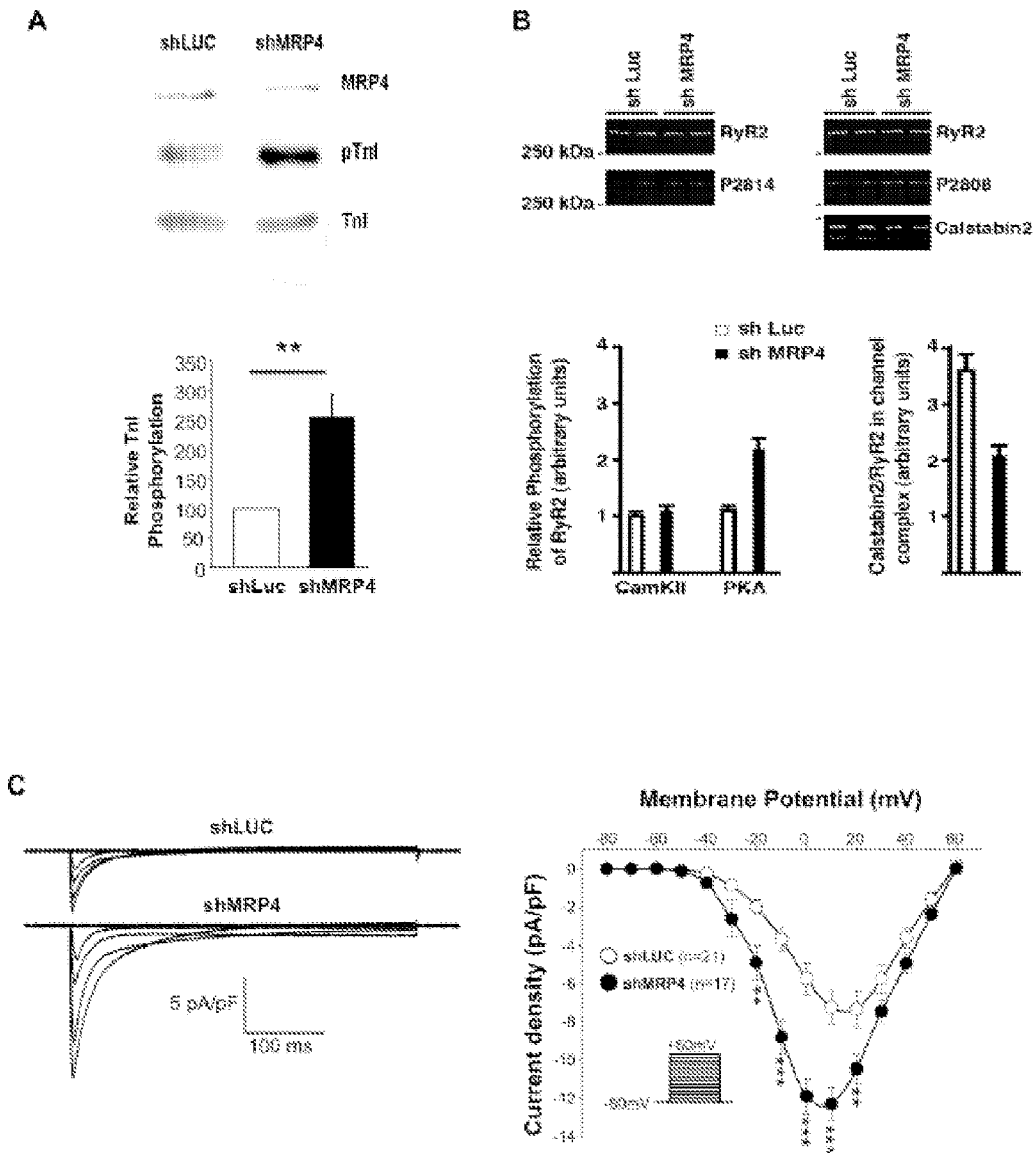

FIG. 2: MRP4 inhibition increases PKA activity in vitro. Adult Rat Ventricular Myocytes (ARVM) were infected with either AdshLuc or AdshMRP4 for 3 days. (A) Representative immunoblot showing a decrease in MRP4 expression and an increase in TnI phosphorylation at the PKA site in ARVMs infected with AdshMRP4. Immunoblots were quantified and normalized to calsequestrin expression. (B). Immunoblots showing an increase in PKA phosphorylation of RyR2 at Ser2808 and a decrease in calstabin2 binding to the RyR2 complex (right panel) but no change in CaMKII phosphorylation at Ser2814 (left panel) in ARVMs infected with Adsh-MRP4. The relative amount of RyR2 phosphorylation was determined by dividing phosphorylation signals by the total amount of RyR2. (C) MRP4 knockdown increases the calcium current in cardiac myocytes. $I_{caL}$ current was recorded in adult rat atrial cardiac myocytes infected with either Ad-ShMRP4 or Ad-shLuc. The current density was significantly increased in cardiacmyocytes infected with Ad-shMRP4 indicating an increase in calcium channels phosphorylation. (p<0.01; *p<0.001).

EXAMPLE

Abstract

Cyclic adenosine 3'-5'-monophosphate (cAMP) is one of the first line messengers that mediate the physiological effect of Gs-coupled receptors. In the heart, upon stimulation of the β-adrenergic receptors, cyclic AMP leads to activation of protein kinase A (PKA) which phosphorylates several key proteins involved in excitation-contraction coupling such as L-type calcium channels, phospholamban, ryanodine receptors and troponin I. This results in PKA-dependent increase in $Ca^{2+}$ current and in calcium handling by the sarcoplasmic reticulum and leads to characteristic positive inotropic and lusitropic effects. Cyclic AMP also directly binds and actives HCN channels which encodes the If current and thus regulates automaticity of the heart. Here we show that MRP4, which is present at the membrane of cardiac myocytes, regulates cAMP signaling pathway in cardiac myocytes, which has impacts on global cardiac structure and function. In isolated rat cardiac myocytes, MRP4 silencing by an adenovirus encoding a MRP4 short hairpin RNA resulted in increased phosphorylation of protein kinase A target proteins. In vivo MRP4 ablation in mice resulted in age-dependent cardiac hypertrophy as well as exacerbated cardiac hypertrophy induced by chronic beta-adrenergic stimulation, apparently associated with an increased activity of PKA. The inotropic and chronotropic effects of milrinone, a PDE3 inhibitor, was dramatically increased in MRP4 deficient mice compared to wild-type suggesting a balance between PDEs and MRP4 for the control of cAMP level in the cardiac myocyte. These findings reveal MRP4-mediated efflux as a new mechanism for regulation of cAMP signaling in cardiac myocytes.

Experimental Procedures

Animal models. MRP4 ablated mice (MRP4 KO) were generated and genotyped as described (Leggas, M. et al. *Mol Cell Biol* 24, 7612-21 (2004). Wild-type and homozygous MRP4-KO mice (8-10 weeks of age) were subjected to left ventricular pressure overload by transverse aortic constriction (TAC), as previously described (Rockman, et al. *Proc Natl Acad Sci USA* 88, 8277-81 (1991). Five weeks after the procedure, the animals were sacrified and heart and body weights were determined. As a model of β-adenergic overstimulation miniosmotic pumps (Alzet) containing (-)-isoproterenol-bitartrate (Sigma Aldrich) (delivering 20 µg/g/day each) were implanted subcutaneously into 10-12 weeks old animals. Determination of heart weights and analysis of gene expression were carried out after 14 days of continuous infusion. Finally, male MRP4 KO mice and WT littermate were subjected to voluntary exercise. The animals were 10-12 weeks at the start of the study. Individual animals were housed in a cage with free access to a 11.5-cm-diameter running wheel with a 5.0-cm-wide running surface equipped with a digital magnetic counter (model BC 1200, Sigma Sport) that is activated by wheel rotation. Daily exercise values for time and distance run were recorded for each exercised animal throughout the duration of the exercise period.

Quantitative Real-time PCR.

Total RNA was prepared with RNeasy Mini kits (Invitrogen) and 1 µg was reverse-transcribed with a standard protocol. One-tenth of the resulting cDNA was amplified by 35 cycles of 30 s at 94° C., 30 s at Tm (60° C. for MRP4, MRP5 and RPL32) and 30 s at 72° C., followed by a final amplification step at 72° C. for 10 min, using 1 unit of BIOTAQ DNA Polymerase (Bioline) and 200 µmol each of the following primers:

```
MRP4-sens:
                            (SEQ ID NO: 1)
5'-GGACACTGAACTAGCAGAATCT-3'

MRP4-antisens:
                            (SEQ ID NO: 2)
5'-GTCGCTGTCAATGATGGTGTT-3'

GAPDH-sens:
                            (SEQ ID NO: 3)
5'-TGGCAAAGTGGAGATTGTTG-3'

GAPDH-antisens
                            (SEQ ID NO: 4)
5'-CATTATCGGCCTTGACTGTG-3'

ANF-sens:
                            (SEQ ID NO: 5)
5'-TTTCAAGAACCTGCTAGACCAC-3'

ANF-antisens:
                            (SEQ ID NO: 6)
5'-CCCTGCTTCCTCAGTCTGCT-3'

Beta-MHC-sens:
                            (SEQ ID NO: 10)
5'-CAATGCAGAGTCGGTGAAGG-3'

Beta-MHC-antisens:
                            (SEQ ID NO: 11)
5'-GCCGCATTAAGTTCTTCTTGTCT-3'

SERCA-sens:
                            (SEQ ID NO: 12)
5'-TGACAATGGCACTTTCTGTTC-3'

SERCA-antisens:
                            (SEQ ID NO: 13)
5'-GCATCCTCAGCAAAGACTGG-3'
```

Gene-specific primers were used to amplify mRNA by qPCR on an Mx4000 apparatus (Stratagene) using the Qiagen SYBR Green master mix. The specificity of each primer set was monitored by analysing the dissociation curve. The sample volume was 25 µl, with 1× (final concentration) SYBR Green PCR master mix, 400 nM gene-specific primers, and 5 µl of template.

Western blot analysis and immunofluorescence. For immunofluorescence, proteins were first incubated with anti-MRP4 (antibody has been described elsewhere (van Aubel, et al. *J Am Soc Nephrol* 13, 595-603 (2002)), anti-MRP5 (Santa Cruz Biotechnology Inc.), or anti-alpha-actinin (Sigma-aldrich) and visualized by applying secondary antibodies directly conjugated to either Alexa Fluor 546 or Alexa Fluor 488 (Invitrogen).

Proteins extraction was performed in a buffer containing protease and phosphatase inhibitors (sigma-aldrich) and Western blotting was performed as previously described. The anti-MRP4 antibody (M4I-80) was kindly provided by Dr.

scheffer (Amsterdam, The Netherlands). The other antibodies were anti-Calsequestrin (ABR), anti-Troponin (Cell signalling), anti-phospho Troponin I (Cell signalling). To measure ryanodine receptors phosphorylation the following protocol was used. Mouse hearts were isotonically lysed in 2.0 ml of a buffer containing 50 mM Tris-HCl (pH 7.4), 150 mM NaCl, 20 mM NaF, 1.0 mM $Na_3VO_4$, and protease and phosphatase (Roche) inhibitors. An anti-RyR antibody (4 μg 5029 Ab) was used to immunoprecipitate RyR2 from 500 μg of heart homogenate. These samples were incubated with antibody in 0.5 ml of a modified RIPA buffer (50 mM Tris-HCl pH 7.4, 0.9% NaCl, 5.0 mM NaF, 1.0 mM Na3VO4, 1% Triton-X100, and protease inhibitors) for 1 hr at 4° C. The immune complexes were incubated with protein A Sepharose beads (Sigma, St. Louis, Ms.) at 4° C. for 1 hr and the beads were washed three times with buffer. Proteins were separated either 6% SDS-PAGE (for RyR) or 15% PAGE (for Calstabin) gels and transferred onto nitrocellulose membranes for 1 hr at 200 mA (SemiDry transfer blot, Bio-Rad). Immunoblots were developed using antibodies against total RyR2 (Affinity Bioreagents, 1:2000 dilution), PKA phosphorylated RyR (P2808, 1:5000) CaMKII phosphorylated RyR (P2814, 1:5000), or calstabin (1:2500). All immunoblots were developed using the Odyssey Infrared Imaging System (LICOR Biosystems, Lincoln, Nebr.) and infrared-labeled secondary antibodies.

Adult ventricular cardiac myocyte culture. Adult rat ventricular myocytes were isolated as previously described (Henaff, et al. *Faseb J* 16, 99-101 (2002)). Adult rat atrial myocytes were isolated as previously described (Abi-Char et al. *J Physiol* 582, 1205-17 (2007)).

Calcium Current measurements and data analysis. The whole-cell configuration of the patch-clamp technique (amplifier, Axoclamp 200A, Axon Instruments) was used to record ICa. Borosilicate glass pipettes (tip resistance: 1 to 2 M[OMEGA]) were filled with a solution containing (in mmol/L) CsCl 130, MgCl2 2, HEPES 10, EGTA 15, glucose 10, and MgATP 3 (pH was adjusted to 7.2 with CsOH). Myocytes infected with Ad-shMRP4 or Ad-shLuc for 3 days were bathed with a solution containing (in mmol/L) NaCl 136.9, KCl 5.4, $CaCl_2$ 2, glucose 10, MgCl2 1.06, and HEPES 10 (pH was adjusted to 7.4 with NaOH). For current recording, NaCl was replaced by an equal amount of tetraethylammonium chloride and KCl was omitted from the solution. Experiments were performed at room temperature (22° C. to 24° C.). Depolarizing voltage pulses were delivered at 0.2 Hz. The amplitude of ICa was calculated as the difference between the peak inward current and the current measured at the end of the test pulse, and its density was obtained by dividing $I_{Ca}$ amplitude by the membrane capacitance. For calcium current inactivation measurement, test pulses for $I_{Ca}$ were preceded by 2-second conditioning pulses. Activation plots were generated by dividing peak $I_{Ca}$ measured at a given potential by the difference between measured and reversal potential. Data on the conductance/voltage activation and inactivation curves were best fitted with a Boltzmann distribution equation: $G/G_{max}=1/[1+\exp((V_{1/2}-V)k)]$ and $I/I_{max}=1/[1+\exp((V_{1/2}-V)k)]$, respectively, where G represents the conductance calculated at membrane potential V, I the amplitude of $I_{Ca}$ at the conditioning potential V, $V_{1/2}$ the potential at which half of the channels are activated or inactivated, and k the slope factor.

Measurement of intracellular $Ca^{2+}$ and $Ca^{2+}$ sparks. Cardiac ventricular myocytes were enzymatically dissociated using standard procedures (Fauconnier, J. et al. Diabetes, 2007). Briefly, mice were euthanized by cervical dislocation, the heart rapidly excised and retrogradely perfused at 37° C. for 6-8 min with a modified tyrode solution (in mM: NaCl 113, KCL 4.7, KH2PO4 0.6, Na2HPO4 0.6, MgSO4 1.2, NaHCO3 12, KHCO3 10, HEPES 10 Taurine 30, pH=7.4) containing 1 mg.ml-1 of liberase (Roche, France). Isolated myocytes were then transferred to the same solution, free of enzyme, containing 1 mM $CaCl_2$.

Cells were loaded for 30 min at RT with Fluo-4 AM (5 μmol/l, Molecular Probes). Cells were then field-stimulated at 1 Hz with a 1-2 ms current pulse delivered via two platinum electrodes, one on each side of the perfusion chamber. Changes in Fluo-4 fluorescence were recorded using an LSM510 Meta Zeiss confocal microscope equipped with a 63× water immersion objective (NA: 1.2). Measurements were performed in line-scan mode (1.5 ms/line) and scanning was carried out along the long axis of the cell. An excitation wavelength of 488 nm was used, and emitted light was collected through a 505 nm long pass filter. The laser intensity used (3-6% of the maximum) had no noticeable deleterious effect on the fluorescence signal or on cell function over the time-course of the experiment. To enable comparisons between cells, the change in fluorescence (ΔF) was divided by the fluorescence detected immediately before the 0.5 Hz stimulation pulse (F0). The SR Ca2+ content was assessed by measuring the amplitude of cytosolic Ca2+ transients induced by the rapid application of caffeine (10 mM). Spontaneous Ca2+ sparks were recorded in quiescent cells following 5 min stimulations in order to reach steady state SR-Ca2+ content. Cell size was estimated at the focal plane in which the largest surface was detected.

Telemetry studies. Long-term telemetric ambulatory ECG measurements were performed in wild type and knock out male mice at 3 months of age. Six-lead restrained ECG monitoring of conscious animals (hamsters and mice) were performed with EasyCG® tools system (EMKA technologies, France) formed by the four sensors of ecgTUNNEL® system platform and a translucent animal sizefitting half-tunnel. Each animal was put inside the tunnel, which was then closed, assuring the animal to be properly restrained. The four wires of the platform were connected to a wireless transmitter and amplifier system (emkaPACK®, EMKA technologies). Telemetric ECG tracing were obtained in conscious mice during quiet awake time at daytime. To minimize the effects of stress, animals were allowed to stay in the restraining system for 5 min before starting ECG recordings. Indeed, direct observation of the animals and ECG traces proved that they were calm and that the heart rate was stable. Six leads of ECG were recorded during 15 to 20 min using specific software (iox®, EMKA technologies): three leads were measured (L1, L2, L3), and three were calculated (aVR, aVL, aVF). Dedicated software (Ecg-auto®, EMKA technologies) was used to measure RR interval, SDNN and HRV index. If needed, raw data were submitted to a 50-Hz notch filter with an automatic setting determined by the software.

Statistics

All quantitative data are reported as means±SEM. Statistical analysis was performed with the Prism software package (GraphPad version 3). One-way ANOVA was used to compare each parameter. Post-hoc t test comparisons were performed to identify which group differences accounted for significant overall ANOVA results.

Results

MRP4 is Expressed at the Membrane of Cardiac Myocytes.

Immunofluorescence analysis of heart tissues revealed the presence of MRP4 at the membrane of both atrial and ventricular myocytes in human and rat. We confirmed the expression of MRP4 protein, which was restricted to the caveolin-enriched membrane fraction, in cardiac proteins extracts separated on a 5% to 40% discontinuous sucrose gradient. MRP5 was also detected in the heart but its expression was restricted to the intimal layer of vessels without clear expression in cardiac myocytes. To determine whether MRP4 regulates the cAMP homeostasis in cardiac myocytes, the intracellular and extracellular cAMP levels were measured in cardiac myocytes treated with forskolin and infected for 3 days with an adenovirus encoding either a MRP4 shRNA, resulting in efficient knock-down of MRP4, or a shRNA encoding luciferase (shLuc) as a negative control. Forskolin (10 μM, 1 hour) increased the intracellular and extracellular levels of cAMP in shLuc treated cells. Silencing MRP4 resulted in a large increase in the forskolin-induced cAMP intracellular level and prevented the increase in the cAMP extracellular level indicating a lack of extrusion of the cyclic nucleotide after MRP4 silencing.

MRP4 Silencing Increased cAMP-Dependent Phosphorylation In Vitro

To study the physiological role of MRP4 we examined the consequence of its silencing on the phosphorylation of several proteins that are PKA targets in cardiac myocytes. MRP4 silencing resulted in hyperphosphorylation of Troponin I at its PKA phosphorylation site Ser23/24. Similarly, analysis of RyR2 phosphorylation revealed a PKA-dependent hyperphosphorylation of Ser2808 in shMRP4 treated cardiac myocytes and this phosphorylation was associated with depletion of the RyR2-stabilizing protein calstabin2 (FKBP12.6). In contrast, MRP4 silencing had no effect on the level of CaMKII phosphorylated RyR2, indicating a specific increase in PKA activity. We also recorded the L-type calcium current, $I_{ca,L}$ a well known target of PKA, in rat atrial cardiac myocytes. In myocytes transduced with the Ad shMRP4, $I_{CaL}$ current density was markedly enhanced compared with shLucinfected myocytes (at +10 mV: $I_{CaL}$ in shMRP4-infected myocytes was $-12.6\pm0.7$ n=19; versus $-7.6\pm0.8$ pA/pF n=21 in shLuc-infected cells, P<0.001). There was a shift toward more negative potential of the current activation in shMRP4 myocytes as observed following cAMP-dependent phosphorylation of calcium current. Taken together, these results indicate that inhibition of MRP4 enhanced cAMP-dependent phosphorylation processes in cardiac myocytes.

PDE Compensates for MRP4 Deletion in Mice

We then measure cardiac parameters that would reflect an increase in catecholaminergic tonus MRP4 in knockout mice. At 3 months of age, no difference was observed between WT and MRP4 KO mice in the fractional shortening ($36\pm1.97$ in WT vs $37\pm2.25$ in MRP4 KO, p=NS) and in the heart rate under basal condition (*RR*(ms): $108\pm4.9$ in WT vs $101\pm3$ in MRP4 KO, p=NS). At the echocardiography examination, the systolic function assayed by measuring the ejection fraction and aortic blow flow were not different between the two groups.

To explain the lack of change in the cardiac function in MRP4 KO mice heart, we tested the hypothesis that activation of PDEs could have compensated for the loss of the transporter. First, mRNA levels of different PDEs were quantified in 3 month-old WT and MRP4 KO mice. PDE3A and PDE4A mRNA levels were significantly increased in the myocardium of MRP4 KO mice compared to WT mice. We also studied the chronotropic effect of the PDE3 inhibitor, Milrinone, in MRP4 KO mice compared to wild-type mice. The chronotropic dose-effect of Milrinone was dramatically enhanced in MRP4 KO mice. The decrease in RR interval following the standard dose of 1 mg/kg milrinone was significantly higher in MRP4 KO mice compared to wild-type mice. Furthermore, while not changing heart rate in wild-type mice, administration of the low dose of 0.1 mg/kg milrinone to MRP4 KO mice resulted in a significant decrease in the RR interval. A similar acceleration of heart rate was observed with a much higher dose (1 mg/kg) of milrinone in wild-type mice. In addition, we have measured the effect of PDE3 inhibition by cilostamide on the contractility of ventricular myocytes isolated from WT and MRP4 KO mice. Cilostamide increased contractility of both WT and MRP4 KO ventricular myocytes but significantly more in the MRP4 KO mice. We have also measured the $Ca^{2+}$ transient under basal condition and after PDE3 inhibition by cilostamide in WT and MRP4 KO mice. Cilostamide increased the amplitude ($\Delta F/F0$), decreased the rate of rise ($\Delta F/F0.ms^{-1}$), the half width and the rate of decay t of the $Ca^{2+}$ transient in ventricular myocytes isolated from MRP4 KO mice. Cilostamide had no effect on the $Ca^{2+}$ transient in myocytes isolated from WT heart. This is consistent with an activation of PDE in 3 month-old MRP4 KO mice that compensates for the ablation of MRP4. Cilostamide by inhibiting PDE3 unmask the increase in cAMP level and its consequences.

MRP4 Ablation is Associated with Progressive Cardiac Hypertrophy.

At 3 months of age, cardiac morphology appeared to be normal. There was no increase in HW/TL ratio (FIG. 1A), in the global histology of the heart (FIG. 1B), in the size of isolated ventricular myocytes (FIG. 1C) and in the echocardiographic parameters (FIG. 1D).

As observed in other models of chronic cAMP deregulation, cardiac hypertrophy develops with age in MRP4 KO mice. Progressive signs of cardiac hypertrophy became significant at 9 months of age in MRP4 KO mice compared to their age-matched controls: The heart weight as well as the HW/TL ratio (FIG. 1A), the size of isolated ventricular myocytes (FIG. 1C), the LVPW thickness and the IVS thickness (FIG. 1D) were significantly greater in 9 month-old MRP4 KO mice than in age-matched WT mice.

To further investigate the consequence of the loss of MRP4 function on myocardial growth and hypertrophy, we studied the response to stimulatory effects of an increase in cAMP level, we tested the effect of chronic β-adrenergic stimulation using miniosmotic pumps delivering isoproterenol (20 μg/g/day) for 2 weeks in 3 month-old MRP4 KO and WT mice. Isoproterenol-induced cardiac hypertrophy was significantly more important in MRP4 KO mice as assessed by a significantly greater HW/TL ratio. These results indicate that the absence of MRP4 plays a role in the mal-adaptative PKA-dependent Gs signaling pathway. Similar results were obtained in another model of hypertrophy induced by thoracic aortic banding (not shown).

These results suggest that, with time or when the β-adrenergic system is over-stimulated, the loss of MRP4 function is no more compensated and that the transporters is coupled to signalling pathways that control myocardial growth.

MRP4 participates to the regulation of SR $Ca^{2+}$ cycling and to regulation of cardiac contractility.

Interestingly, the fractional shortening was greater in 9 month-old MRP4 KO mice compared to age-matched WT indicating an increase in contractility. In addition, the shortening of ventricular myocytes isolated from 9 month-old MRP4 KO mice was greater than the shortening of myocytes from 9-month-old WT mice.

We thus looked at SR $Ca^{2+}$ cycling in ventricular myocytes isolated from 3- and 9-month-old WT and MRP4 KO mice. In 3-month-old animals, in basal conditions, there was no difference in the $Ca^{2+}$ transient kinetics between WT and MRP4 KO mice. At that stage, there was no difference in Sparks frequency and kinetics (data not shown). However in 9-month old animals, despite no change in the SR load and in the amplitude (ΔF/F0) of the $Ca^{2+}$ transient, the rate of rise (ΔF/F0.ms$^{-1}$) and rate of decay t of the transient were accelerated in MRP4 KO mice than in WT mice. In addition, the sparks frequency and their spatial distribution (full width at half maximum) were markedly increased whereas their amplitude ΔF/F was decreased without difference in their kinetics. Interestingly, RyR2 was PKA hyper-phosphorylated on its Ser2808 and this was associated with depletion of the RyR2 stabilizing protein calstabin 2 (FKBP12.6). No difference was observed in phosphorylation of Ser 2814.

These results suggest that MRP4 could participate in the β-adrenergic regulation of SR $Ca^{2+}$ cycling in the heart.

Conclusion

Our study demonstrates, to our knowledge for the first time, that the cAMP level in cardiac cells can be regulated by extrusion via the multidrug resistance-associated protein MRP4. This new mechanism that regulates cAMP homeostasis is coupled to several cAMP-mediated signalling pathways involved in both the physiology and the growth of the cardiac myocyte.

MRP5 was previously detected in the human heart and its expression was increased in ischemic and dilated cardiomyopathy. Here we demonstrate that MRP4 is mainly expressed at the membrane of cardiac myocytes whereas MRP5 is present in total heart extracts but mainly in the endothelial layer of coronary vessels in agreement with our previous results.

We also demonstrated that MRP4 is an element of a highly inter-dependent system to control cAMP signalling. The cardiac contractility, the heart rate are preserved in young MRP4 ablated mice. The SR $Ca^{2+}$ cycling data, both the transients and sparks characteristics are normal and the cAMP/PKA-dependent targets, such as RyR2 and TNI, are not hyper-phosphorylated indicating a compensatory mechanism. Our observation that the positive chronotropic and inotropic effects of the PDE3 inhibitors milrinone and cilostamide are largely increased in MRP4 ablated mice, compared to wild-type mice, support the concept of a balance between PDEs and MRP4 for the control of the cAMP levels in cardiomyocytes. It also provides evidence that the respective contributions of PDE or MRP in the control of cAMP homeostasis should be dependent on the activity of the counterpart element in the cascade. In our in vitro experiments, MRP4 silencing led to hyper-phosphorylation of PKA target proteins that was not observed in young MRP4 KO mice. In the in vitro experiment, MRP4 silencing was obtained rapidly (i.e., around 48 hours) which could have been a too short delay to allow an effective adjustment in the activity/expression of PDEs. This should explain the important effect of MRP4 inhibition in this model. On the other hand, the relative paucity in the cardiac phenotype of young MRP4 KO mice and the increased effect PDE3 inhibitors in these mice indicate that the activity of PDE3 is enhanced to counteract cyclic nucleotide signalling pathways activation due to MRP4 deficiency. This is concordant with an adaptative feedback mechanism to limit the deleterious effect of the loss of cAMP extrusion via the transporter. The impact of MRP4 ablation might thus have been hindered by PDE hyper-activation in young MRP4 KO mice under basal conditions. This observation is another indication that MRP4 is a constitutive physiological mechanism such as its suppression must be compensated. It should be mention that cyclic nucleotides extrusion by MRPs is an energy-dependent mechanism whereas degradation by PDEs does need energy. This is in favour of an activation of MRPs in stress conditions such as during adrenergic stress and is supported by a greater trophic effect of isoproterenol in MRP4 deleted mice compared to control mice.

With aging or under pathological stress such as chronic high catecholamine cardiac stimulation, the compensatory mechanism of MRP4 suppression might be overwhelmed resulting in the increase in cAMP-dependent phosphorylation of cardiac myocyte and the development of hypertrophy. This is indicated by the progressive cardiac hypertrophy as well as an increased SR $Ca^{2+}$ leak associated with an increased phosphorylation of RyR2 at Ser2808 in older MRP4 KO. Moreover, MRP4 ablation in mice led to an exacerbation of the effects of chronic β-adrenergic stimulation which was observed in young mice, suggesting that a limit in PDE3 compensation was reached upon stimulation. Noteworthy, the phenotype of the PDE4D3 KO mice resembles the phenotype of the MRP4 KO mice. They both develop an age-dependent hypertrophic process with hyper-phosphorylation of RyR2.

Surprisingly, despite cardiac hypertrophy, the contractile function of the aged MRP4 deleted mice was increased. Both the fractional shortening, measured by echocardiography, and the cell shortening measured on isolated ventricular myocytes were greater for MRP4 KO mice than for WT. The enhanced contractility of isolated cardiac myocytes from MRP4 deficient mice excluded an effect on the vascular bed.

It is well-established that intracellular effectors of cyclic nucleotides are compartmentalized in macromolecular complexes, and MRP4 is an additional partner of these complexes. As in smooth muscle cells, we found that MRP4 is localized in caveolin-enriched membrane fractions. Caveolae/lipid rafts are specialized membrane microdomains in which multimolecular complexes of signalling molecules are compartmentalized by interacting with caveolin-1. The MRP4 C-terminal protein sequence contains a consensus PDZ domain-binding motif, suggesting that MRP4 could interact tightly with other partners of membrane signalling complexes. Indeed, in gut epithelial cells, MRP4 is associated with the CFTR Cl-channel. This indicates that MRP4 may act in specific subcellular domains and thereby modulate an initial activation step of cyclic nucleotide-mediated signal transduction. Our results also suggest that MRP4 can interact with other partners of the β-adrenergic signalling cascade or which channels which however remains to be analyzed. Interestingly, it has been reported that the integrity of caveolae/lipid rafts is necessary for the normal coupling between β1-AR and calcium channels. The β1-AR cardiac-specific overexpressing mice develop cardiac hypertrophy and heart failure indicating that at least in this condition, MRP4 and PDEs are not active enough to compensate for the increased cAMP level. However, we demonstrate that chronic stimulation of the β adrenergic system leads to more important deleterious effects in mice deleted for MRP4 suggesting that in normal conditions MRP4 plays a role in maintaining cardiac function.

Our data provide evidence that MRP4 and PDEs are both important in maintaining cAMP level and MRP4 is a new element to take into account when analyzing cardiac cAMP homeostasis.

These results indicate that MRP4 regulates cyclic-nucleotides signalling pathways in cardiomyocytes. MRP4 inhibition enhances the cardiomyocyte response to cAMP. This comprises electrophysiological activity and also cardiomyocyte growth. MRP4 inhibition may thus enhance the favourable short-term effect of cAMP in cardiomyocyte, notably the chronotropic and inotropic responses. Such effect will have therapeutic consequences in heart failure and in cardiogenic schock. On the other hand, long-term activation of MRP4 may fight against the chronic pro-hypertrophic effect of cAMP. This will allow the treatment and the prevention of pathological cardiac hypertrophy.

REFERENCES

Throughout this application, various references describe the state of the art to which this invention pertains. The disclosures of these references are hereby incorporated by reference into the present disclosure.

Assender J W, Southgate K M, Hallett M B, Newby A C. Inhibition of proliferation, but not of Ca2+ mobilization, by cyclic AMP and GMP in rabbit aortic smooth-muscle cells. Biochem J. 1992 Dec. 1; 288 (Pt 2):527-32.

Barouch L A, Harrison R W, Skaf M W, Rosas G O, Cappola T P, Kobeissi Z A, Hobai I A, Lemmon C A, Burnett A L, O'Rourke B, Rodriguez E R, Huang P L, Lima J A, Berkowitz D E, Hare J M. Nitric oxide regulates the heart by spatial confinement of nitric oxide synthase isoforms. Nature. 2002 Mar. 21; 416(6878):337-9.

Boerth N J, Dey N B, Cornwell T L, Lincoln T M. Cyclic GMP-dependent protein kinase regulates vascular smooth muscle cell phenotype. J Vasc Res. 1997 July-August; 34(4): 245-59.

Brummelkamp T R, Bernards R, Agami R. A system for stable expression of short interfering RNAs in mammalian cells. Science. 2002 Apr. 19; 296(5567):550-3.

Chen Z S, Lee K, Kruh G D. Transport of cyclic nucleotides and estradiol 17-beta-D-glucuronide by multidrug resistance protein 4. Resistance to 6-mercaptopurine and 6-thioguanine. J Biol. Chem. 2001 Sep. 7; 276(36):33747-54. Epub 2001 Jul. 10.

Choi V W, Samulski R J, McCarty D M. Effects of adenoassociated virus DNA hairpin structure on recombination. J. Virol. 2005 June; 79(11):6801-7.

Colas P, Cohen B, Jessen T, Grishina I, McCoy J, Brent R. (1996) Genetic selection of peptide aptamers that recognize and inhibit cyclin-dependent kinase 2. Nature, 380, 548-50.

Cole et al., Monoclonal Antibodies and Cancer Therapy, Alan R. Liss, Inc., 1985, pp. 77-96).

Cote R J, Morrissey D M, Houghton A N, Beattie E J Jr, Oettgen H F, Old L J. Generation of human monoclonal antibodies reactive with cellular antigens. Proc Natl Acad Sci USA. 1983 April; 80(7):2026-30.

Desgranges P, Caruelle J P, Carpentier G, Barritault D, Tardieu M. Beneficial use of fibroblast growth factor 2 and RGTA, a new family of heparan mimics, for endothelialization of PET prostheses. J Biomed Mater Res. 2001; 58(1):1-9.

Dzau V J, Braun-Dullaeus R C, Sedding D G. Vascular proliferation and atherosclerosis: new perspectives and therapeutic strategies. Nat. Med. 2002 November; 8(11):1249-56.

Elbashir S M, Harborth J, Lendeckel W, Yalcin A, Weber K, Tuschl T. Duplexes of 21-nucleotide RNAs mediate RNA interference in cultured mammalian cells. Nature. 2001 May 24; 411(6836):494-8.

Hannon G J. RNA interference. Nature. 2002 Jul. 11; 418 (6894):244-51.

Jayasena S. D. (1999) Aptamers: an emerging class of molecules that rival antibodies in diagnostics. Clin Chem. 45(9):1628-50.

Jedlitschky G, Burchell B, Keppler D The multidrug resistance protein 5 functions as an ATP-dependent export pump for cyclic nucleotides. J Biol. Chem. 2000 Sep. 29; 275(39): 30069-74.

Kohler G, Milstein C. Continuous cultures of fused cells secreting antibody of predefined specificity. Nature. 1975 Aug. 7; 256(5517):495-7.

Kriegler, A Laboratory Manual," W.H. Freeman C.O., New York, 1990.

McDonald L J, Murad F. Nitric oxide and cyclic GMP signaling. Proc Soc Exp Biol Med. 1996 January; 211(1):1-6.

McManus M T, Sharp P A. Gene silencing in mammals by small interfering RNAs. Nat Rev Genet. 2002 October; 3(10): 737-47.

Maglich J M, Parks D J, Moore L B, Collins J L, Goodwin B, Billin A N, Stoltz C A, Kliewer S A, Lambert M H, Willson T M, Moore J T. Identification of a novel human constitutive androstane receptor (CAR) agonist and its use in the identification of CAR target genes J Biol. Chem. 2003 May 9; 278(19):17277-83

Mitani A, Nakahara T, Sakamoto K, Ishii K. Expression of multidrug resistance protein 4 and 5 in the porcine coronary and pulmonary arteries. Eur J. Pharmacol. 2003 Apr. 11; 466(1-2):223-4.

Murry, "Methods in Molecular Biology," vol. 7, Humana Press, Inc., Cliffton, N.J., 1991.

Novak K. Cardiovascular disease increasing in developing countries. Nat Med. 1998 September; 4(9):989-90.

Rybalkin S D, Yan C, Bornfeldt K E, Beavo J A. Cyclic GMP phosphodiesterases and regulation of smooth muscle function. Circ Res. 2003 Aug. 22; 93(4):280-91. Review.

Silberbach M, Gorenc T, Hershberger R E, Stork P J, Steyger P S, Roberts C T Jr. Extracellular signal-regulated protein kinase activation is required for the anti-hypertrophic effect of atrial natriuretic factor in neonatal rat ventricular myocytes. J Biol. Chem. 1999 Aug. 27; 274(35):24858-64.

Sinnaeve P, Chiche J D, Gillijns H, Van Pelt N, Wirthlin D, Van De Werf F, Collen D, Bloch K D, Janssens S. Overexpression of a constitutively active protein kinase G mutant reduces neointima formation and in-stent restenosis. Circulation. 2002 Jun. 18; 105(24):2911-6.

Sunahara R K, Dessauer C W, Gilman A G. Complexity and diversity of mammalian adenylyl cyclases. Annu Rev Pharmacol Toxicol. 1996; 36:461-80.

Tuerk C. and Gold L. (1990) Systematic evolution of ligands by exponential enrichment: RNA ligands to bacteriophage T4 DNA polymerase. Science. 3; 249(4968):505-10.

Tuschl T, Zamore P D, Lehmann R, Bartel D P, Sharp P A. Targeted mRNA degradation by double-stranded RNA in vitro. Genes Dev. 1999 Dec. 15; 13(24):3191-7.

Wu Z, Asokan A, Samulski R J. Adeno-associated virus serotypes: vector toolkit for human gene therapy. Mol. Ther. 2006 September; 14(3):316-27. Epub 2006 Jul. 7.

The invention claimed is:

1. A method for treating cardiac hypertrophy, comprising administering an agent that stimulates Multidrug Resistance Protein 4 activity to a subject in need thereof.

2. A method for inhibiting the hypertrophic response of cardiomyocytes, comprising administering an agent that stimulates Multidrug Resistance Protein 4 activity to a subject in need thereof.

3. A method for treating chronic heart failure, comprising administering an agent that stimulates Multidrug Resistance Protein 4 activity to a subject in need thereof.

* * * * *